United States Patent [19]
Papalos

[11] 4,089,894
[45] May 16, 1978

[54] SULFONATED ALKYLPHENOXY 2 TO 5-CARBON-ATOM ALKANOIC ACIDS AND SALTS

[75] Inventor: John George Papalos, Ledgewood, N.J.

[73] Assignee: Diamond Shamrock Corporation, Cleveland, Ohio

[21] Appl. No.: 654,069

[22] Filed: Feb. 2, 1976

[51] Int. Cl.$^2$ .................. C07C 143/52; D06P 5/04
[52] U.S. Cl. ...................... 260/507 R; 260/501.19; 260/501.21; 8/89 R; 8/169
[58] Field of Search ........... 260/507 R, 501.21, 501.19

[56] References Cited

U.S. PATENT DOCUMENTS

| | | | |
|---|---|---|---|
| 2,178,829 | 11/1939 | Bruson et al. | 260/512 R |
| 2,337,924 | 12/1943 | Platz et al. | 260/512 R |
| 3,116,321 | 12/1963 | Horn et al. | 260/507 R |
| 3,636,016 | 1/1972 | McGuire | 260/507 R |
| 3,809,717 | 5/1974 | Daeuble et al. | 260/512 R |

*Primary Examiner*—Nicky Chan
*Attorney, Agent, or Firm*—Theodore J. Dettling

[57] ABSTRACT

The novel compounds, sulfonated alkylphenoxy alkanoic acids containing 2 to 5 carbon atoms in the acid moiety and their salts. In dyeing nylon textiles with acid dyes, barre is reduced by using these novel compounds as a dye leveler.

5 Claims, No Drawings

SULFONATED ALKYLPHENOXY 2 TO 5-CARBON-ATOM ALKANOIC ACIDS AND SALTS

BACKGROUND OF THE INVENTION

This invention relates to sulfonated alkylphenoxy alkanoic acids containing 2-5 carbons in the acid moiety and their salts, and to the use of these compounds as dye levelers in dyeing synthetic polyamide textiles with acid dyes to alleviate barre.

In dyeing synthetic polyamide textiles such as fibers, fabrics, or garments (hereafter collectively called "nylons" or "nylon textiles") with acid dyes, there often is obtained barre or streakiness in the dyed textile due to inherent physical and/or chemical differences existing in the yarns from which the textile has been made. For further information about the causes and manifestations of barre reference is made to U.S. Pat. No. 3,619,122 and *American Dyestuff Reporter*, Feb. 12, 1968, pgs. 42–47.

To prevent or minimize barre to an acceptable degree, a variety of anionic surfactants have been employed as dye levelers in the dyeing of nylon textiles with acid dyes. One of the earliest class of anionic surfactants used were the mixed fatty alcohol sodium sulfates. Subsequently, alkyl sulfonate and alkyldiaryl sulfonate surfactants were recommended. More recently, more complex anionics have been alleged to prevent barre, for example: sulfonated sulphones derived from a variety of hydroxy-substituted aryl compounds in U.S. Pat. No. 3,536,438, dialkyl sulfosuccinates in U.S. Pat. No. 3,619,122, alkane-or alkene-amido-benzene-sulphonics in U.S. Pat. No. 3,713,768, and monosulfonated alkylphenoxy glycerol in U.S. Pat. No. 3,809,717. Also, alkyl-substituted diphenyl ether sulfonates, believed to have the general formula shown in U.S. Pat. No. 3,127,441, have been used.

In spite of the abundance of work done to identify anionic surfactants capable of minimizing or preventing barre, a need still exists for new dye levelers considering the great number of different acid dyes employed, the fact that they are typically used in combinations, and the variety of nylons textiles being dyed. In many instances less-than-satisfactory barre effects are tolerated because a dye leveler suitable from both an economic and a performance standpoint is unavailable.

SUMMARY OF THE INVENTION

Considering this state of the art, it is an object of the present invention to provide new anionic surfactants that function as dye levelers and are effective in minimizing or preventing barre effects when used in the dyeing of a variety of nylon textiles with different acid dyes.

This object and other objects and advantages, which will become apparent from the following description and examples, are provided by the novel sulfonated alkylphenoxy alkanoic acids and their salts hereinafter described, and by their utilization in dyeing nylon textiles with acid dyes.

DESCRIPTION OF THE PREFERRED EMBODIMENTS

The new sulfonated alkylphenoxy alkanoic acids and their salts that it has been discovered function as dye levelers in dyeing nylons with acid dyes have the general formula:

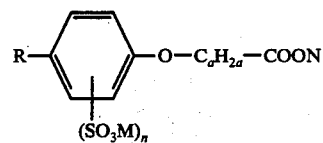

wherein:
R is an alkyl radical having an average of 8–20 carbon atoms;
M and N are independently selected from the group consisting of hydrogen, sodium, potassium, ammonium, and substituted ammonium;
$n$ is a number of from 1 to 2; and
$a$ is a number of from 1 to 4.

The alkyl radical R in the invention compounds may be straight chained or branched, may be saturated or unsaturated, and may be comprised of a mixture of alkyl groups having differing numbers of carbon atoms. Because of its ready availability and low cost, invention compounds produced from dodecyl phenol are preferred.

When $a$ is 2, 3 or 4 the radical, $C_aH_{2a}$, may be straight chained or branched. Thus, —$C_aH_{2a}$—COON, when N is H, can be:

—$CH_2COOH$, an acetic acid radical;
—$CH_2$—$CH_2$—COOH, a 3-propionic acid radical;

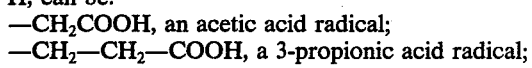

a 2-propionic acid radical;
—$CH_2$—$CH_2$—$CH_2$—COOH, a 4-butanoic acid radical;

—CH—COOH,
   |
   $C_2H_5$ a 2-butanoic acid radical;
—$CH_2$—$CH_2$—$CH_2$—$CH_2$—COOH, a 5-pentanoic acid radical; and so forth.

The substituents M and N in the invention compounds may be the same or different. Thus, in the acid form of the compounds both M and N are hydrogen; while in the double salt form M and N are either sodium, potassium, ammonium or substituted ammonium (by which is meant water-soluble amines such as ethyl amine, dimethyl amine, diethanol amine and the like), and usually are identical. Finally, in the mono or acid salt form (i.e. where either M or N is hydrogen), usually N is hydrogen.

Lastly, in the invention compounds $n$ is 1 or 2, or some fractional number between 1 and 2 when the invention compound comprises a mixture of the monosulfonated and disulfonated compounds, for example, 1.5 when equal parts of each are present. Best dye leveling has been obtained when $n$ is 1.

The invention compounds are readily prepared, as illustrated and described in more detail in the following examples, by first sulfonating a phenol having a para-substituted alkyl group having an average of 8–20 carbon atoms with enough sulfonating agent (chlorosulfonic acid, oleum and the like) to give the desired average number of sulfonic acid groups. This reaction is well known, as shown for example in U.S. Pat. Nos.

2,249,757 and 3,707,352, and is most easily done in solution using an organic solvent inert to the reaction such as ethylene dichloride, 1,2-dichloropropane and the like. The resulting sulfonated intermediate is then reacted with a chloroalkanoic acid having 2 to 5 carbon atoms to produce the invention phenoxy ether compound in one of the following ways depending upon the position in the acid component of the invention compound of the ether valency bond relative to the carboxyl group. Phenoxy 2-alkanoic acid compounds are prepared by first neutralizing the sulfonated intermediate with an aqueous sodium or potassium hydroxide solution, and then admixing about a stoichiometric quantity of the 2-chloroalkanoic acid slowly over a period of 30–60 minutes. Additional aqueous sodium or potassium hydroxide is added concurrently with the chloroacid to neutralize the HCl generated and at a rate that maintains the reaction at a pH of at least 8. Phenoxy 3-, 4-, or 5-alkanoic acid compounds, on the other hand, are prepared in an anhydrous organic medium employing synthesis procedure like that illustrated in Example 7. The resulting phenoxy ether product, which can be recovered and purified by conventional means, will be in the form of the double salt of the alkali metal hydroxide used. The monosalt or the acid form is produced by reacting the double salt with a suitable acid, such as HCl, in an amount required to give the desired product, and is purified and isolated by conventional means. When the ammonium or substituted ammonium salt is desired, ammonium hydroxide or a water-soluble amine is used in the synthesis in place of the sodium or potassium hydroxide. Alternatively, the acid form of the invention compound can be reacted with the desired ammonium compound. The syntheses of sulfonated alkylphenoxy compounds by procedures similar to those described herein are disclosed in U.S. Pat. Nos. 2,178,830, 3,707,352 and 3,809,717.

As previously described, the invention compounds have been discovered to be effective dye levelers for nylon textiles dyed with acid dyes, being effective anti-barre agents for a variety of nylon-dye combinations. Generally, the nylon textiles, acid dyes, and dyeing procedures utilized are conventional.

Thus, the nylon textiles to be dyed may be in the form of fibers (either staple or continuous), fabrics (woven, nonwoven, knitted and the like), or finished textile goods; and may consist of only synthetic polyamide, or may consist of blends of the polyamide with other textile materials (such as polyesters, polyacrylonitriles, wool, cotton, and the like) compatible with the dyes and the dyeing conditions used for the nylon.

The acid dyes employed, generally, may be any of those normally used for dyeing nylon, as for example, those belonging to the azo, anthraquinone, quinophthalone, phthalocyanine or triphenylmethane classes of dyes or the nitro or formazane dyestuffs, which optionally may contain complex-bound metals, such as copper, nickel, chromium or cobalt.

The quantity of the invention sulfonated alkylphenoxy alkanoic acid compounds employed usually will be the minimum necessary to provide an acceptably uniform and streak-free dyed textile (dye-leveling quantity). Generally, depending on a number of interrelated factors, such as type of nylon, type and quantity of the dye, dyeing conditions and the like, acceptable alleviation of barre can be achieved with about 0.25 to 4.0 parts by weight of the invention compound per 100 parts by weight of the nylon textile being dyed. In most cases, from about 0.5 to 1.0 part will be optimum from a cost/performance standpoint. Since the invention compounds are facilely produced, marketed, and used in industrial dyeing as aqueous dispersions, the double salts, being most soluble, will normally be employed. The monosalt and acid forms of the invention compounds, however, are equally suitable when their lesser solubilities do not cause problems. Because of their lower costs, the acetic acid ethers and the alkali metal salts are normally preferred for dye leveling. While only one of the invention compounds is usually employed, mixtures of two or more may be used. Further, for some dyeings, other anionic surfactants may advantageously be used in conjunction with the invention compounds.

With respect to the dyeing process, the invention dye-leveler compounds like those of the prior art, normally, are most effective if added to the dye bath containing the nylon textile before the dye, and preconditioning the textile for some finite period, such as 5 to 30 minutes, before dye addition. Dyeing temperatures normally vary between 60° and 120° C, with 80°–100° C being typical. When the textile is preconditioned, temperatures of about 25°–60° C are usual, followed by higher temperatures, such as 80°–120° C, after the dye addition. During dyeing, the bath typically is maintained at a pH of about 6 to 8, and is lowered to about 4.0 or less near the end of the cycle if more complete dye exhaust and improved washfastness is desired. Control of pH is usually achieved with compounds such as acetic acid, formic acid, dilute sulfuric or phosphoric acid, ammonium sulfate, sodium acetate and the like. Other materials often used in acid dyeing may also be used with the invention compounds, as for example: nonionic surfactants to improve fabric wetting or control the degree of dye dispersion; organic water-miscible solvents, such as isopropanol, to predisperse the acid dyes or assist in fabric wetting; and chelating agents, such as ethylenediamine tetra-acetic acid, to tie up iron and other polyvalent metal ions that can adversely effect the dyeing process or product quality. After dyeing, the nylon textile is normally washed with water before being dried.

EXAMPLES 1–4

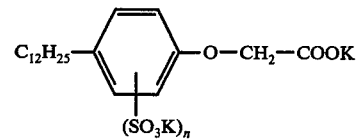

EXAMPLE 1

A compound of the above formula wherein $n$ is 1 is produced as follows: 116 parts (1 mole) of chlorosulfonic acid is added over two hours to an agitated solution of 272 parts of p-dodecylphenol (1 mole based on OH number) and 400 parts of ethylene dichloride maintained at 0°–25° C. The resulting mixture is agitated at 10°–25° C for about 6 hours under a slight vacuum to remove HCl. Then, 521 parts of 15% aqueous KOH (1.4 moles) is added with stirring while maintaining the temperature at 30°–50° C. Next, 720 parts of 15% aqueous KOH (1.93 moles) and 188 parts of a 50% aqueous solution of monochloroacetic acid (1 mole) are concurrently added to the stirred reaction mixture within a 30 minute period while maintaining the temperature at 68°–72° C, care being taken to add the KOH at a rate sufficient to maintain the reaction mixture at a pH of 8 or more (measured on a 5% solution). The reaction mixture is refluxed (70°–75° C) for 6 hours with vigorous agitation, cooled to 60° C, and the pH adjusted with HCl to 10.0 ± 0.5 (measured on a 5% solution). After standing 1 hour at 40°–50° C, the reaction mixture divides into two layers and the top aqueous layer is discarded. 360 parts of water are added to the bottom organic layer and its pH adjusted to 10 ± 0.5 using either 10% HCl or 15% KOH. All of the ethylene dichloride is azeotropically distilled off and the batch cooled to 60° C. Lastly, 200 parts of isopropanol and 100 parts of melted polyethylene glycol (600 molecular weight) are admixed in and the solids adjusted, if necessary, with water to give a product having a total solids of 30 ± 1%. The product is storage stable and usable as a leveling agent in dyeing nylon textiles.

EXAMPLE 2

A compound of the above formula wherein $n$ is more than 1 is produced using the procedure of Example 1 and increasing the chlorosulfonic acid from 1.0 to 1.25 moles and the first increment of KOH from 1.4 to about 1.65 moles.

EXAMPLE 3

A compound of the above formula wherein $n$ is more than 1 is produced using the procedure of Example 1 and increasing the chlorosulfonic acid from 1.0 to 1.5 moles and the first increment of KOH from 1.4 to about 1.9 moles.

EXAMPLE 4

A compound of the above formula wherein $n$ is more than 1 is produced using the procedure of Example 1 and increasing the chlorosulfonic acid from 1.0 to 1.75 moles and the first increment of KOH from 1.4 to about 2.15 moles.

EXAMPLE 5

The sulfonated dodecylphenoxy potassium acetates of Examples 1–4 were evaluated as dye levelers in a series of dye tests employing an Ahiba laboratory dyeing machine, 10 gram samples of a nylon tiger stripe test fabric, and the following dyestuffs:

| VIOLET DYE | |
|---|---|
| 0.15% (o.w.f.) | Acid Red #299 |
| 0.02% (o.w.f.) | Acid Yellow #159 |
| 0.08% (o.w.f.) | Nylosan Blue NBLF |
| BROWN DYE | |
| 0.8% o.w.f. | Acid Blue #232 |
| 0.25% o.w.f. | Acid Yelow #49 |
| 0.05% o.w.f. | Acid Red #99 |
| 0.05% o.w.f. | Acid Blue #247 |
| BLUE DYE | |
| 0.25% o.w.f. | Acid Blue #122 |
| GREEN DYE | |
| 0.25% o.w.f. | Acid GREEN #25 |

The dyeing procedure used for each test consisted of: preparing 300 mls of a dyebath containing 2% o.w.f. of ammonium sulfate and either 0.5% or 1.0% o.w.f. of the dye leveler, setting the bath at 120° F, entering the fabric sample and running ten minutes at 120° F, adding the dyestuff and running 10 minutes at 120° F, raising the bath temperature about 2°/minute to 212° F and running for 60 minutes more, adding 0.5% o.w.f. of acetic acid and running for 30 minutes at 212° F, rinsing the fabric with warm water, spin-extracting the rinse water, and air drying the fabric.

The results of the dye-leveling tests are compiled in the Table. In the tests, the improvement in color uniformity (alleviation of barre or barre coverage) over a blank (no dye-leveler) was ascertained independently for each dyestuff. Color uniformity ratings were based on an arbitrary scale of 1–5, with 1 being the poorest and 5 the best. The color uniformity ratings shown in the Table are the average of five ratings by different textile chemists. From this data it can be seen that all the invention compounds of Examples 1–4 function as dye levelers in dyeing nylon textiles with a variety of acid dyes, and that the compound having one sulfonate group per molecule (Example 1) exhibits better dye-leveling than the invention compounds having an average of more than one sulfonate group.

| Dye Leveler | 5 Dye Tests | | | |
|---|---|---|---|---|
| | Violet | Brown | Blue | Green |
| Example 1 | | | | |
| 0.5% o.w.f. | 4.0 | 3.4 | 3.0 | 4.0 |
| 1.0% o.w.f. | 4.0 | 4.0 | 3.5 | 4.5 |
| Example 2 | | | | |
| 0.5% o.w.f. | 3.5 | 3.0 | 2.0 | 3.5 |
| 1.0% o.w.f. | 4.0 | 3.5 | 3.0 | 4.0 |
| Example 3 | | | | |
| 0.5% o.w.f. | 3.0 | 3.0 | 2.0 | 3.0 |
| 1.0% o.w.f. | 3.5 | 3.0 | 2.5 | 3.5 |
| Example 4 | | | | |
| 0.5% o.w.f. | 3.0 | 3.0 | 2.0 | 3.0 |
| 1.% o.w.f. | 3.5 | 3.5 | 3.0 | 3.5 |
| Blank | | | | |
| (No dye leveler) | 2.0 | 1.0 | 1.0 | 1.0 |

EXAMPLE 6

The double potassium salt of dodecylphenoxy 2-propionic acid containing one sulfonate group is prepared by the same procedure used in Example 1 for the acetic acid ether homolog except that 108 parts of 2-chloropropionic acid (1 mole) is used and it is added as 100% material (rather than as 50% aqueous solution); and the product is recovered and purified in an organic solution. More particularly, the product is isolated and purified by the following procedure: To 2100 parts of the mixed water/ethylene dichloride/product dispersion there is admixed 400 parts of water, 200 parts of isopropanol, and 100 parts of melted polyethylene glycol (600 mol. wt.). The resulting admixture is allowed to stand overnight to permit formation of an aqueous layer (1360 parts) and an organic layer (1440 parts). After being separated, 80 parts more of isopropanol is admixed into the organic layer. The resulting solution had a total solids of 44% and a pH of 9.5 (measured on a 5% aqueous solution of the product).

In a beaker dye test employing 0.10% o.w.f. Acid Green #25 dye and the nylon tiger stripe test fabric, the 2-propionic acid ether compound gave at 1% o.w.f. a dyed fabric having less barre than a similarly dyed fabric employing 0.5% o.w.f. of the Example 1 compound as the dye leveler.

EXAMPLE 7

The double potassium salt of monosulfonated dodecylphenoxy 3-propionic acid is produced as follows: To 390 parts of potassium dodecylphenol monosulfonate (1 mole) dispersed in 300 parts of xylene there is added 56 parts of KOH powder (1 mole) and the mixture is heated about 8 hours, and the water formed in producing the potassium phenolate is azeotropically distilled off. Next, 108 parts of 3-chloropropionic acid (1 mole) and 56 parts of powder KOH (1 mole) are added simultaneously with vigorous stirring and the reaction continued under reflux (150° C.). After 6 hours, heating and agitation is discontinued and 100 ml of 10% aqueous NaCl is admixed in and the batch is allowed to stand quiescent for 4 hours to permit separation into two layers. After discarding the bottom aqueous layer, there is admixed into the top organic layer 300 ml. of water, and the resulting solution heated to distill off the xylene azeotropically. The resulting product is an aqueous slurry containing a dispersion of the dipotassium salt of dodecylphenoxy 3-propionic acid monosulfonate.

When clear solutions are desired, there is added about 6% by weight of melted polyethylene glycol (Mol. Wt of 600), based on total weight of the batch, and isopropanol in an amount sufficient to yield a product having about 30% total solids.

The invention alkylphenoxy alkanoic acids or their salts may also be employed in other applications where sulfonate- and/or carboxylate-containing surfactants are used. For example, they may be used as detergents dispersing agents, emulsifying agents for latex polymerizations, textile wetting agents, penetrating agents, leather tanning agents, textile scouring agents, and the like. For some of these applications, the presence of both a sulfonate and a carboxylate group (or the corresponding acid groups) in the same molecule can be advantageous.

What is claimed is:

1. A compound having the formula

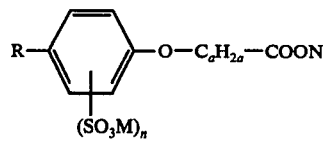

wherein:
R is an alkyl group having 8–20 carbon atoms;
M and N are independently selected from the group consisting of hydrogen, sodium, potassium, ammonium, ethyl ammonium, dimethyl ammonium, and diethanol ammonium;
$n$ is a number of from 1 to 2; and
$a$ is a number of from 1 to 4.

2. The compound of claim 1 wherein $a$ is 1.
3. The compound of claim 1 wherein $n$ is 1.
4. The compound of claim 1 wherein R is an alkyl group having 12 carbon atoms.
5. The compound of claim 4 wherein $a$ is 1 and M and N are potassium or sodium.

* * * * *